US 8,696,803 B1

(12) United States Patent
Knapp, III et al.

(10) Patent No.: US 8,696,803 B1
(45) Date of Patent: Apr. 15, 2014

(54) AIR PERMEABLE SCENTING LATEX FORMULATION FOR SPRAY APPLICATION ON AN AIR FILTER

(71) Applicant: Scentco, LLC, Thomasville, GA (US)

(72) Inventors: Joseph F. Knapp, III, Thomasville, GA (US); Karl Jones, West Milford, NJ (US); Robert Reardon, Glen Cove, NY (US)

(73) Assignee: Scentco, LLC, Thomasville, GA (US)

( * ) Notice: Subject to any disclaimer, the term of this patent is extended or adjusted under 35 U.S.C. 154(b) by 0 days.

(21) Appl. No.: 13/905,022

(22) Filed: May 29, 2013

(51) Int. Cl.
*B01D 46/00* (2006.01)

(52) U.S. Cl.
USPC .............................................. 96/222; 96/226

(58) Field of Classification Search
USPC .......... 96/222, 223, 226, 227; 422/1, 4, 5, 26, 422/27, 28, 41, 42, 43, 243, 255, 291, 292, 422/293, 306; 516/1–3, 9–11, 20–22, 31, 516/77, 98, 99, 198
See application file for complete search history.

(56) References Cited

U.S. PATENT DOCUMENTS

| | | | | |
|---|---|---|---|---|
| 3,567,119 A | * | 3/1971 | Wilbert et al. ...................... 239/6 |
| 3,939,099 A | * | 2/1976 | Tusa et al. ........................ 512/2 |
| 3,994,439 A | * | 11/1976 | Van Breen et al. .............. 239/54 |
| 4,476,180 A | * | 10/1984 | Wnuk ............................ 428/220 |
| 4,904,639 A | * | 2/1990 | Hallam .............................. 512/4 |
| 6,838,492 B2 | | 1/2005 | Maleeny et al. |
| 6,929,681 B2 | | 8/2005 | Maleeny et al. |
| 7,135,169 B2 | | 11/2006 | Maleeny et al. |
| 2002/0004033 A1 | * | 1/2002 | Sorgenfrey ...................... 424/43 |
| 2004/0053791 A1 | * | 3/2004 | Langer et al. .................. 508/154 |
| 2007/0020223 A1 | * | 1/2007 | Maleeny et al. .............. 424/76.2 |
| 2009/0078119 A1 | * | 3/2009 | Buckley ........................... 96/222 |

* cited by examiner

*Primary Examiner* — Duane Smith
*Assistant Examiner* — Sonji Turner
(74) *Attorney, Agent, or Firm* — Buskop Law Group, PC; Wendy Buskop

(57) ABSTRACT

An aqueous scenting formulation formulated for spray application on an air scenting device for use in an HVAC system to form an air permeable barrier film which slows the rate of water evaporation and provides long lasting freshening or scenting of air flowing through the device with minimal blockage of air flow through the HVAC system having a latex in the amount of from 10 percent to 50 percent by weight of the aqueous scenting formulation, wherein the latex consists of a vinyl/polyvinyl acetate, and wherein the mean particle size of the vinyl/polyvinyl acetate in the latex is from 75 microns to 90 microns in diameter; a surfactant selected from the group consisting of: non-ionic and anionic surfactants and mixtures thereof; and a fragrance material.

11 Claims, 1 Drawing Sheet

AIR PERMEABLE SCENTING LATEX FORMULATION FOR SPRAY APPLICATION ON AN AIR FILTER

FIELD

The present embodiments generally relate to an air permeable and aqueous scenting formulation that can be applied as a spray to simultaneously provide a scent while reducing water evaporation as air travels through air filters used in mechanical forced air heating, ventilating and air conditioning ("HVAC") systems to provide a freshened or scented air while filtering the air.

BACKGROUND

A need has existed for an aqueous, sprayable formulation that can be quickly deposited on an air filter for an HVAC system for simultaneously providing moisture control and air permeability while releasing a fragrance or scent into the air path.

The present embodiments meet this need.

BRIEF DESCRIPTION OF THE DRAWINGS

The detailed description will be better understood in conjunction with the accompanying drawings as follows.

Figure 1:
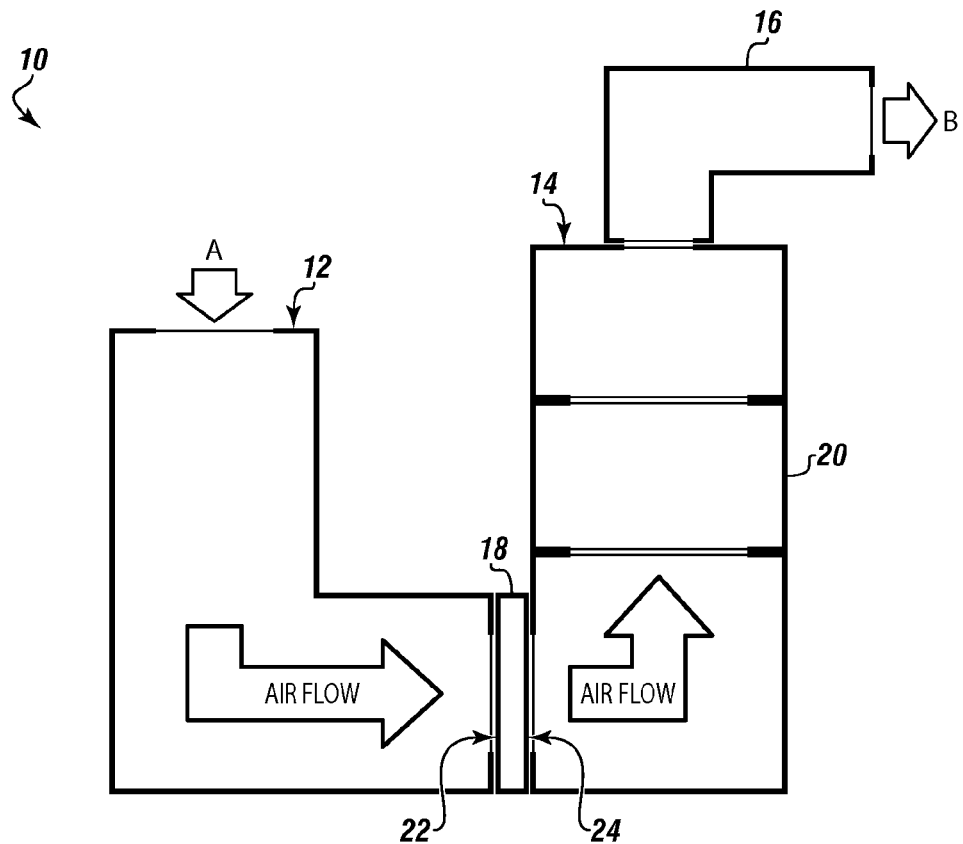
FIG. 1 depicts an HVAC system usable with the formulation according to one or more embodiments.

The present embodiments are detailed below with reference to the listed Figures.

DETAILED DESCRIPTION OF THE EMBODIMENTS

Before explaining the present formulation in detail, it is to be understood that the formulation is not limited to the particular embodiments and that it can be practiced or carried out in various ways.

A need exists for a formulation that can be deposited on an air filter that provides fragrance and moisture control without impeding air flow.

The embodiments relate to a formulation wherein a releasable fragrance is incorporated into a vinyl/polyvinyl acetate latex with a solvent and a surfactant and the resulting aqueous scenting formulation can then be sprayed onto an air filter, forming a fragranced polymer film.

The fragranced polymer film, when applied in a thickness from 1 micron to 50 microns on an air filter, such as a cellulose air filter, of an HVAC unit, forms a treated filter with an air permeable barrier that permits at least 80 percent of the air to continue through the air filter, while simultaneously reducing a rate of water evaporation through the HVAC filter by at least 10 percent as compared to un-treated HVAC filters, and while simultaneously releasing fragrance into the air flowing through the treated air filter.

An embodiment of the invention can include a formulation for a fragranced latex which when applied to one of various filter substrates, such as cellulose, polymer, polymer/urethane, or metal, the latex quickly adheres to the substrate, forming an encapsulating polymer film curing to a tackiness in less than 10 minutes at the latex/air interface.

The embodiments relate to an aqueous scenting formulation formulated for spray application on air filters for use in an HVAC system.

The embodiments relate to an aqueous scenting formulation formulated for spray application on air filters for use in an HVAC system without the need for a propellant other than air.

The embodiments relate to an air filter fully coated, that is encapsulated, with the formed aqueous scenting formulation.

The embodiments relate to an HVAC air filter having at least one surface, such as 50 percent of the filter, covered with the aqueous scenting formulation defined herein.

The aqueous scenting formulation can contain from 10 weight percent to 50 weight percent of a water based vinyl acetate acrylic polymer adhesive latex. This type of latex can be similar to the ones available from Lanco and Harris Corporation of Orlando, Fla. as product number JB-100 and has a use level range from 10 percent to 14 percent.

The water based vinyl acetate acrylic polymer adhesive latex can contain 40 weight percent to 70 weight percent water.

The aqueous scenting formulation polymer size can have a mean particle size from 75 microns to 90 microns in diameter.

To the water based vinyl acetate acrylic polymer adhesive latex can be added 0.1 weight percent to 10 weight percent of a low foaming, non-ionic surfactant compatible with anionic particles that additionally act as a wetting agent.

To the water based vinyl acetate acrylic polymer adhesive latex can also be added 0.1 weight percent to 10 weight percent of a solvent selected from the group: a glycol, an ethanol, methanol, other alcohols, and combinations thereof. When a glycol is used, hexylene glycol can be used in amounts from 8 percent to 10 percent, such as hexylene glycol from GJ Chemical of Somerset, N.J.

To the water based vinyl acetate acrylic polymer adhesive latex, a liquid fragrance capable of dissolving in the solvent can be added from 10 weight percent to 40 weight percent.

To make the formulation, the water based vinyl acetate, acrylic polymer adhesive latex, low foaming non-ionic surfactant, solvent and liquid fragrance can be blended simultaneously using high shear mixing for periods of time to form an emulsion latex aqueous scenting formulation using a time period not to exceed 12 hours of mixing.

The formed emulsion latex aqueous scenting formulation can include a solids content of vinyl/polyvinyl acetate and liquid fragrance content greater than 50 percent by weight of the vinyl/polyvinyl acetate.

This aqueous scenting formulation emulsion latex can be applied in a thickness from 1 micron to 50 microns on at least a portion of a filter of an HVAC unit to form a treated filter with an air permeable barrier film, allowing at least 80 percent of the air through the treated filter while reducing a rate of water evaporation through the treated filter by at least 10 percent over a non-treated filter, while simultaneously releasing fragrance into air flowing through the treated filter for up to 15 days.

In embodiments, the aqueous scenting formulation can have as the surfactant, a solvent free anionic/nonionic grind aid surfactant.

In embodiments, the aqueous scenting formulation surfactant can be selected from the group consisting of: low foaming, non-ionic surfactants compatible with anionic particles, non-ionic, dimethyl octynediol surfactants, ethoxylated alkyl phenols, non-onic, octoxynol 9 surfactants, non-ionic, polysorbate 20 and mixtures thereof. Polysorbate 20 is also commercially sold as TWEEN® from Uniqema Americas, LLC of Wilmington, Del. and can be used in amount from 3 weight percent to 6 weight percent.

In embodiments, the aqueous scenting formulation can include 0.1 weight percent to 8 weight percent of a rheological modifier.

In embodiments wherein the aqueous scenting formulation uses a rheological modifier, the rheological modifier can be gums, clays, cellulosic material, sugars, starches, algins, such as a gelatin, a polymeric thickener, and mixtures thereof.

In embodiments, the aqueous scenting formulation can include 0.1 weight percent to 0.5 weight percent of an antimicrobial agent. The antimicrobial agent can include an antifungal component, an antibacterial component or combinations thereof, for reducing the presence of microbes on an air filter coated with the aqueous scenting formulation. In embodiments, the coated air filter can reduce the content of microbes flowing into a facility.

In embodiments, the aqueous scenting formulation can be a spray application which functions as a non-aerosol spray.

In embodiments, the aqueous scenting formulation can include 0.1 weight percent to 1 weight percent based on the total formulation of a mildewcide.

In embodiments, the aqueous scenting formulation surfactant can contain an additional 0.1 weight percent to 2 weight percent based on the total surfactant weight percent of an additional detergent, wetting agent, emulsifier, foaming agent, or dispersants.

In embodiments, the aqueous scenting formulation can additionally include from 0.1 weight percent and 8 weight percent of a pigment, such as a food grade dye, a filler, such as talc, malodor scavengers or combinations of these components.

The term "liquid fragrance" as used herein refers to a liquid formed from essential oils, such as lavender oil, combined with an organic chemical, such as ethyl butyrate, which together create an identifiable smell, such as bubble gum, in this example. Over 400 liquid chemical combinations can be utilized to form the liquid fragrances that are usable in embodiments.

The term "rheological modifier" refers to a component that thickens and increases viscosity of the formed aqueous scented material. In an embodiment, the rheological modifier can increase the viscosity by 1 percent to 8 percent of the aqueous scented material. In embodiments, the viscosity of the scented material is low enough that it doesn't clog the nozzles of a spray gun or spray apparatus used to deposit the aqueous scented material on the filter.

Once formed, this aqueous scenting formulation can have the structure of a film and act as a barrier which slows the rate of water evaporation from the HVAC system.

The term "HVAC", as used herein refers to heating, ventilation and air conditioning systems, such as those for houses, office buildings, or facilities. The abbreviation "GRS", as used herein refers to grams.

Turning now to the Figures, FIG. 1 illustrates a conventional forced air HVAC system wherein a housing 10 can have an inlet end 12 and an outlet end 14 connected to an air outlet ducting 16 which disperses filtered air into the surrounding environment. Mounted in the housing 10 can be a filter 18 and a fan or blower assembly 20 for controlling the ambient air flow through the housing 10 in the direction indicated by arrows A and B from the inlet end 12 of the housing through the filter 18 from the filter's upstream facing surface 22 to its downstream facing surface 24 and then to the outlet end 14 of the housing 10 and into the air outlet ducting 16 for distribution into the surrounding environment.

The aqueous scenting formulation can be formed on the filter 18 at the air interface.

Figure 2:
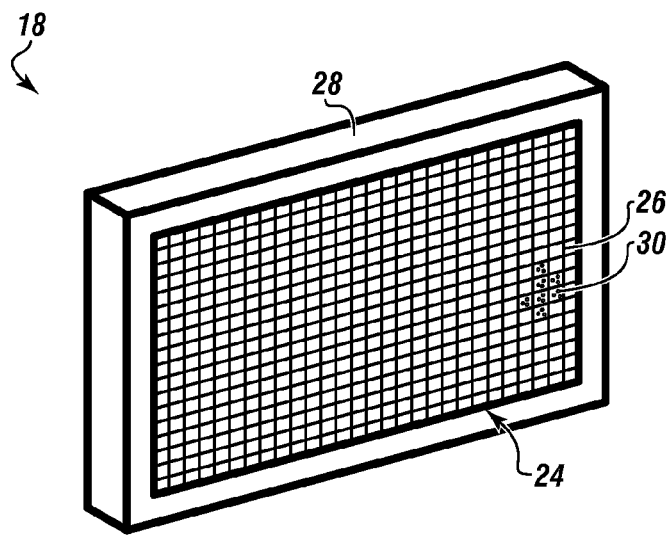
FIG. 2 depicts a filter with the aqueous scenting formulation disposed thereon according to one or more embodiments.

FIG. 2 shows the filter 18, which can be a standard air filter of a commercially available type typically provided for use in an HVAC system, such as that depicted in FIG. 1. The filter 18 in conventional form is comprised of a filter medium 26, which can be a fibrous air permeable filter medium, such as a textile material, fiberglass, or other woven fibers that arrest particles in the interstices of the filter medium 26.

Typically a suitable rigid or semi-rigid frame 28 surrounds the periphery of the filter medium 26 for holding the filter medium 26 in position. The frame can be cardboard. The aqueous scenting formulation 30 can be applied directly to the filter medium 26.

The aqueous scenting formulation 30 can be applied in spray form directly onto the filter medium from any suitable spray application device.

In this regard, it should be noted that the spray application device can be a simple button operated spray jar or a more technically advanced pump arrangement such as a MARK IV® spray pump system, commercially available from Saint-Gobain Calmar Inc., having a head assembly with interchangeable orifice caps to provide nozzles of varying dimensions for accurate adjustment of the spray droplet size. The spray application device can be used to spray the aqueous scenting formulation in thicknesses ranging from 1 micron to 50 microns onto the surface of the filter medium of the air filter.

The aqueous scenting formulation can be disposed on the filter medium by pumping the aqueous scenting formulation through pre-selected sized orifices formed in the interchangeable orifice cap in a back and forth motion, or in an all in one spray, then the coating is allowed to tackify.

For example, a head assembly for use in the spray pump system used to supply a "wide" spray providing fine sized particle diameters of about 70 microns to about 75 micron particle diameters can employ an orifice cap structured with an 0.020 inch orifice size and 0.008 inch depth.

As another example, a head assembly for use in the spray pump system used to supply a "medium" spray providing medium sized particle diameters of about 75 microns to about 80 micron particle diameters can employ an orifice cap structured with an 0.013 inch orifice size and 0.010 inch depth.

As a third example, a head assembly for use in the spray pump system to supply a "narrow" spray providing large sized particle diameters of about 85 microns to about 90 micron particle diameter can employ an orifice cap structured with a 0.013 inch orifice size and 0.010 inch depth.

The aqueous scenting formulation can adhere to the filter medium at application locations on the surface of the filter medium.

The aqueous scenting formulation can be applied in essentially any desired arrangement or in a random configuration, shape or form about a surface of the filter medium, which can be the upstream facing surface, the downstream facing surface, or combinations thereof. In practice, the aqueous scenting formulation can be sprayed onto the filter medium at locations around a generally central portion of the filter.

The articles formed with the sprayed-on, fragranced latex formulations can include filters used in central home heating and air conditioning systems.

In formulating the formulation, it is to be noted that the vinyl/polyvinyl acetate component can be affected by the physical dynamics that transform liquid lattices into films include the chemical formulation, particle sizes of the formulation, surface tension generated by the chemical formulation, drying rates of the applied material, and conditions of the air around the film, including temperature and humidity.

Latex vinyl/polyvinyl acetates and vinyl/polyvinyl acetate acrylics transform into a film during the drying through a well-known process.

During application to an air filter, sprayed latex particles can become attached to filter fibers, which can be fiber glass, and quickly form a surface encapsulating film.

The surface encapsulating film can present wetting forces and contact angles between droplets of the spray and fibers of the substrate.

The latex formulation can not only provide adhesion to the substrate, but also simultaneously provide wetting between the latex droplets and filter fibers. This wetting retards the droplet tendency to collect in larger droplets due to the action of gravity.

Spray droplet size can be regulated by the rheological characteristics of the fragranced polymer latex in combination with the orifice characteristics employed in the spray application device, which in an embodiment can be a spray pump.

It should be noted that droplet size is important in regulating the initial and long range perception of fragrance throughout a facility when the scent or fragrance is emitted from an air filter in an HVAC system.

Based on studies conducted utilizing a MARK IV® spray pump head assembly, commercially available from Saint-Gobain Calmar Inc., having interchangeable orifice caps to adjust the droplet size sprayed onto air filters, it has been determined that spraying of small, fine latex particles, from 70 microns to 75 microns in diameter produce a maximum initial burst of fragrance from a treated filter installed in a standard HVAC system for about 2 days to about 3 days and then fades. A need exists for at least 15 days of fragrance, which is achieved with the novel formulation.

It has been determined that spraying of larger size latex particles, having diameters from 75 microns to 85 microns on a filter substrate results in a longer lasting perception of fragrance and a slower sustained fragrance release over a longer duration lasting from 5 days to 8 days. The present embodiments provide such a latex with longer life.

It has been determined that spraying of even larger size latex particles, having diameters from 85 microns to 90 microns results in a still longer duration of fragrance perception in a facility, from about 12 days to about 21 days.

With regard to the preparation of the scenting formulations of the present invention, these formulations are created in a manner such that once applied and tackified as a film, the film does not create a significant air obstruction and, therefore, does not impede air flow or air heating/cooling efficiencies when sprayed on an air filter in an HVAC system.

Furthermore, when scenting formulations containing fragrance materials only, without any additives, sprayed onto air filters they do not form a uniform spray pattern of fine droplets and may not be absorbed by or adhere well to the fibers of the filter. As a result, the fragrance materials in the aqueous scenting formulation will drip and evaporate rapidly and the effect of the fragrance will be lost in only a few hours.

These formulation problems have been overcome herein by forming a polymer latex adding a surfactant, and a solvent to improve cure, as well as the scenting component.

In this manner, the polymer latex is an emulsion that creates a uniform spray pattern of small droplets of the overall formulation including the fragrance, disposing the fragrance evenly on the fiber, and causing the fragrance to adhere to the fibers such as fiberglass fibers of an air filter as well as act as a fixative to retard the rate of evaporation of water passing through the filter.

In an embodiment, the aqueous scenting formulation can be prepared by forming mixtures of fragrance materials which can be fragrance oils, such as rose oil, lavender oil, or a calming fragrance, and blending into a latex matrix of vinyl/polyvinyl acetate to which is added a surfactant and a solvent. Once sprayed, the blend forms the film with the fragrance oil uniformly dispersed throughout the blend and the sprayed film as small droplets.

In an embodiment, gum, such as zanthanum gum, can also be included in the mixture to produce formulations which are similar in appearance and properties to glue and which, when applied to a filter, either by spray or by the drop disposition, adheres to the filter medium.

The film that forms on the filter medium is air permeable and, thus, although the film to retard the rate of evaporation of the fragrance oils and water, the film permits air to pass through the film enabling the fragrance from the spray to release, in a timed release manner.

This formulation has the advantage of avoiding premature coalesce into a gelatinous phase of the formulation.

This formulation has the advantage of providing a continuous phase surface tension that decreases the pressure forces need for particle/particle lamination forming the film on the substrate.

Air freshening or scenting formulations for use in the present invention can be prepared by a process comprising forming a colloidal dispersion of a latex type emulsion of a vinyl/polyvinyl acetate.

The vinyl/polyvinyl acetate polymer can be predissolved in a suitable solvent such as polyvinyl alcohol, that is 98 percent to 99 percent hydrolyzed, and having a high molecular weight, such as those designated as CAS#9002-89-5 and made by Alfa Aesar GmbH & Co.

The surfactant component is incorporated in the dispersion to improve clarity, to control the rate of evaporation and/or to aid in the dispersion of the fragrance material blended or dispersed in the solution.

With regard to suitable surfactants for use in the scenting formulations, a wide variety of non-ionic and/or cationic surfactants advantageously can be employed in formulating these formulations.

Furthermore, the surfactant should have a low odor profile so that it will not interfere with the odor profile of the fragrance. Examples of surfactants can include: nonoxynol-6m, such as SURFONIC® N60 from Huntsman Petrochemical Corporation; nonoxynol-9, such as IGEPAL® CO630 sold by Rhodia Operations; nonoxynol-10, such as TERGITOL® NP-10 sold by Union Carbide Corporation; ceteth-2, such as BRIJ® 72 sold by Uniqema Americas, LLC; and steareth-20, such as BRIJ® 78 sold by Uniqema Americas, LLC. Non-ionic phenols and ethoxylated alcohols are other surfactants that can also be used.

The surfactants for use in preparing the aqueous scenting formulations can include anionic/nonionic grind aid surfactants, such as SURFYNOL® CT-131 which is sold by Air Products & Chemicals, Inc. Other surfactants can be an ethoxylated alkyl phenol such as a nonionic octoxynol-9, such as TRITON® X-100, which is a surfactant product sold by Union Carbide Corporation or a nonionic, polysorbate 20 product, such as TWEEN® sold by Uniqema Americas, LLC.

The surfactant can be a solvent free anionic/nonionic grind aid surfactant, such as SURFYNOL® CT-171 sold by Air Products & Chemicals, Inc., which has been found to provide both effective pigment wetting and dispersing characteristics as well as latex stabilizing effects in the formulations of the present invention. Other surfactants that can be used herein include low foaming, non-ionic surfactants compatible with anionic particles, such as the SURFYNOL® TG sold by Air Products & Chemicals, Inc. and non-ionic, dimethyl octynediol surfactants, such as SURFYNOL® 82 also sold by Air Products & Chemicals, Inc.

The aqueous scenting formulation can release fragrant material, under typical ambient household conditions, or commercial facility conditions, for a predetermined period of time ranging from about one day to several months or more.

With regard to fragrance materials suitable for use in the aqueous scenting formulations, it should be noted that any desirable known scenting or fragrance materials can be employed to produce such formulations provided that the fragrance is compatible with the aqueous mixture and the formulas are balanced to eliminate partial fractionation.

Examples of scents or fragrances for use in producing the aqueous scenting formulations of the present invention include, but are not limited to, citrus scented fragrances, vanilla scented fragrances, apple scented fragrances, floral scented fragrances, and the like. Scents or fragrances used can be those similar to fragrances available from Flavor & Fragrance Specialties, Inc.

In embodiments, the aqueous scenting formulations can serve as a bactericide. In additional embodiments, an antimicrobial agent can be added to the aqueous scenting formulation.

Antimicrobial agents can be antibacterial, antifungal or combinations thereof. The antimicrobial agent can be added in amounts from 0.1 weight percent to 0.5 weight percent based on the total formulation to discourage the growth of microorganisms that can adversely affect the odor or stability of the formulation.

Examples of suitable anti-microbial agents for inclusion in the formulations of this invention can include: chlorohexidine gluconate; propylene glycol, methyl paraben, propyl paraben, imidazolidinyl urea, such as ABIOL™ sold by 3V Inc., stabilized chlorine dioxide sold under the trade name ANTHIUM DIOXCIDE® made by E. I. Du Pont de Nemours and Company, oxazolidine, such as BIOBAN® CS-1246 sold by The Dow Chemical Company, substituted triazine, such as BIOBAN® GK, oxazolidine blend, such as BIOBAN® N-95, blends of morpholine derivatives, such as BIOBAN® P-1487, silica hydrogel, such as BRITESORB® A 100 sold by PQ Corporation, 5-bromo-5-nitro-1,3 dioxane, 10 percent solution in propylene glycol, such as BRONIDOX® L made by COGNIS Corporation, 2-bromo-2-nitropropane-1,3-diol, such as BRONOPOL sold by Inolex Chemical Co., DMDM hydantoin, such as CUSTOM® DMDM by Custom Ingredients, Inc., DMDM hydantoin, such as DANTOGARD® sold by Lonza Inc., liquid preservative systems, such as EMERCIDE® 1199 sold by COGNIS Corporation, phenoxyethanol, such as EMERESSENCE® 1160 sold by COGNIS Corporation, blends of morpholine derivatives, such as DOWICIL® sold by The Dow Chemical Company, Diazolidinyl urea and parabens, such as GERMABEN® made by Sutton Laboratories, Inc., diazolidinyl urea, such as GERMALL® made by Sutton Laboratories, Inc., diazolidinyl urea and iodopropynyl butylcarbamate, such as GERMALL® PLUS sold by Sutton Laboratories, Inc., imidazolidinyl urea, such as GERMALL® 115 by Sutton Laboratories, Inc., iodopropynyl butyl carbamate, such as GLYCACIL® sold by Lonza Inc., DMDM hydantoin, such as GLYDANT® sold by Lonza Inc., DMDM hydantoin and iodopropynyl butyl carbamate, such as GLYDANT PLUS® sold by Lonza Inc., DMDM hydantoin and iodopropynyl butyl carbamate, such as GLYDANT PLUS® Liquid by Lonza Inc., hexahydrotriazine, such as GROTAN® by Troy Corporation, dimethyloldimethylhydantoin sold under the trade name LANODANT DM™ sold by R.I.T.A Corporation, propylene glycol (and) DMDM hydantoin (and) methylparaben, such as LANOPLEX™ 1 sold by R.I.T.A Corporation, propylene glycol (and) DMDM hydantoin (and) methylparaben (and) propylparaben, such as LANOPLEX™ 2 sold by R.I.T.A Corporation, Propylene glycol (and) DMDM hydantoin (and) methyl paraben, such as PARGON® sold by The McIntyre Group, Ltd., propylene glycol (and) DMDM hydantoin (and) methyl paraben (and) propyl paraben, such as PARGON® II sold by The McIntyre Group, Ltd., phenoxyethanol (and) DMDM hydantoin (and) methyl paraben (and) propyl paraben, such as PARGON® III sold by The McIntyre Group, Ltd., Para-chloro-meta-cresol, such as PCMC™ sold by Howard Hall Div. R.W. Greeff and Co., Inc., phenoxyethanol (and) DMDM hydantoin (and) iodopropynylbutyl carbamate, such as PHENAGON® PDI sold by Rhodia Operations, methylparaben, such as RITA METHYLPARABEN™ sold by R.I.T.A Corporation, methylchloroisothiazolinone (and) methylisothiazolinone, such as RITA PRESER™ 150 sold by R.I.T.A Corporation, propylparaben, such as RITA PROPYLPARABEN™ sold by R.I.T.A Corporation, 2-mercaptopyridine-1-oxide, sodium salt sold under the trade name Sodium OMADINE® sold by Arch Chemicals, Inc., cetyl trimethyl ammonium bromide, such as BROMAT® sold by Zeeland Chemicals, Inc., sodium hydroxymethylglycinate, such as SUTTOCIDE® A sold by Sutton Laboratories, Inc., Tris (hydroxymethyl)nitromethane, such as TRI NITRO® sold by The Dow Chemical Company, proprietary bactericides, such as TROYSAN® by Troy Corporation and usable in amounts from 0.1 percent to 0.5 percent.

Additionally, amine adducts, such as TROYSAN® 174 also from Troy Corporation, are usable herein as well as 2(Hydroxymethyl)amino-2-methyl-1-propanol, 78 percent, such as TROYSAN® 186 sold by Troy Corporation, amine adducts, such as TROYSAN® 186-II sold by Troy Corporation, 2-[(Hydroxymethyl)amino]-2-methyl-propanol, 100 percent, such as TROYSAN® 192 sold by Troy Corporation, amine adducts, such as TROYSAN® 192-II and TROYSAN® 198 sold by Troy Corporation. Tin complexes, such as such as TROYSAN® 364 sold by Troy Corporation, Hydantoin, such as such as TROYSAN® 395 sold by Troy Corporation, formulations of 1,2 Bendiasothiazolin,3-one (BIT), such as TROYSAN® 586 sold by Troy Corporation.

Additional amide additives that are usable herein include MERGAL® K10N, and POLYPHASE® SA 27.polysorbate available by Troy Corporation.

Other optional additives for inclusion in the formulations, in addition to the anti-bacterial or anti-microbial agents, can include adding 0.1 weight percent to 0.1 weight percent based on the total formulation of a mildewcides, with or without the anti-bacterial/anti-microbial agents, as desired. In embodiments, the aqueous scenting formulation can include 0.1 weight percent to 0.5 weight percent based on the total formulation of a mildewcide.

Examples of mildewcidal agents which can be incorporated in the formulations of the present invention can include, but are not limited to the following mildewcides: 2-n-octyl-4-isothiazolin-3-one ("Skane M-8"); 3-iodo-2-propanyl butyl carbamate ("Polyphase AF-1'"'); tetra-chloroisophthalonitril ("Nopcocide N-96"); N-trichloromethyl thiophthalimide ("Fungitrol 11'"', "Folpet"); 2-(thicyanonethylthio) benzothiazole ("Busan"); tributyl tin oxide ("TBTO"); 1,2 benzisothiazolin-3-one, aqueous amine solution ("Proxel"); butadiene sulfone; butadiene polysulfone; 3,5 dimethyl tetrahydro 1,3,5,2H thiadiazine-2-thione ("Cansan S"); 2,4 dichloro-6-(O-chloroanilino)-s-triazine ("Fugritrol Alpha"); 3,5-dibromo-3'-trifluoromethyl salicanilide ("Fluorophene"); 2,3,5,6-tetrachloro-4-(methylsulfonyl)pyridine ("Dow S-13"); diiodomethyl p-tolyl salons ("Amical"); 5,6-dichloro benzoazolinone-2 ("Irgasan FP"); 3,5,3',4 tetrachloro salylanilide ("Irgasan BS-200"); cyclohexylsulfamate ("Onyxide 172"); dinitro-1-methyl heptyl phenyl crotonate ("Karathane"); 2-(4-thiazolyl)benzimidazole ("Metasol TK-100"); p-toluene sulfonamide; sulfur; n-(3-chlorophenyl) itaconmide; tetra methyl thiuram disulfide ("Tuex"); trans 1,2 bis(n-propylsulfonyl)ethylene ("Vancide PA"); n-trichloromethyl tetrahydro phthalimide and zinc.

Rheological agents can be added to the formulation in amounts from 0.1 weight percent to 8 weight percent.

The rheological agents are used for thickening the overall formulation while simultaneously controlling thixotropic characteristics.

Examples of rheological agents for use in embodiments of the aqueous scenting formulation can be additives such as gums, including guar and guar derivatives, clays including montmorillonite, bentonite, vermiculite clays and the like, cellulosics including carboxymethylcellulose, polyanionic cellulosics (PACs) sold by Akzo Nobel under the tradename Gabrosa and the like, dextrins, algins, polymeric thickeners including anionic, hydrophobically modified alkali soluble acrylic latexes (HASE), such as ACUSOL® formerly sold by Rhom and Haas Company; thickeners based on polyurethanes, such as TAFIGEL® sold by Munzing Chemie GmbH and NUVIS™ sold by Sasol Servo B.V. and like rheological agents, and mixtures thereof.

In embodiments, the aqueous scenting formulation surfactant can additionally contain 0.1 weight percent to 2 weight percent of detergents, wetting agents, emulsifiers, foaming agents, and dispersants.

The following examples are intended for illustration purposes only, and should not be deemed to limit the scope of the invention as defined in the appended claims.

Example 1

An aqueous scenting formulation in accordance with the present invention having a "Fresh & Clean" scent was formulated in the laboratory by mixing the following ingredients:

| | |
|---|---|
| 130 GRS | LANCO JB-100 (POLYVINYL ACETATE BLEND) |
| 80 GRS | HEXYLENE GLYCOL |
| 1 GRS | TROYSAN 174 |
| 48 GRS | TWEEN 20 (POLYSORBATE 20) |
| 610 GRS | WATER |
| 1 GRS | BITREX @ 1% WATER |
| 130 GRS | FRESH & CLEAN FRAG. (SIMPLY CLEAN CONC. KVJSCENTS #5) |
| 1000 GRS | |

In preparing this composition, the water content of the composition was initially introduced into a main batching vessel at ambient temperature. Then, the vinyl acetate acrylic polymer adhesive latex was added to the water with moderate stirring. Thereafter, remaining ingredients (the surfactant and then the fragrance) were added with continued mixing with an overhead mixer until a homogenous blend was produced.

The resulting aqueous scenting formulation containing the vinyl acetate acrylic polymer adhesive latex emulsion was sprayed onto woven filters and was found to spray well with minimal droplet coalescence and running. After the spray-dried-on filters were installed in a standard home HVAC system, full home air freshness/scent was detected for up to 15 days. The resulting aqueous scenting formulation meets all regulatory guidelines and has unique ratios that provide unexpected optimized strength and longevity without the need to add ingredients.

The resulting aqueous scenting formulation meets all regulatory guidelines and has unique ratios that provide unexpected optimized strength and longevity without the need for additional ingredients.

Example 2

An aqueous scenting formulation in accordance with the present invention having a "Tropical Fruity" scent was formulated in the laboratory by mixing the following ingredients:

| | |
|---|---|
| 130 GRS | LANCO JB-100 (POLYVINYL ACETATE BLEND) |
| 80 GRS | HEXYLENE GLYCOL |
| 1 GRS | TROYSAN 174 |
| 53 GRS | TWEEN 20 (POLYSORBATE 20) |
| 610 GRS | WATER |
| 1 GRS | BITREX @ 1% WATER |
| 125 GRS | TROPICAL FRUITY FRAG. (TROPICAL FILTER BRZ KVJSCENTS #1) |
| 1000 GRS | |

In preparing this composition, the water content of the composition was initially introduced into a main batching vessel at ambient temperature. Then, the vinyl acetate acrylic polymer adhesive latex was added to the water with moderate stirring. Thereafter, remaining ingredients (the surfactant and then the fragrance) were added with continued mixing with an overhead mixer until a homogenous blend was produced.

The resulting aqueous scenting formulation containing the vinyl acetate acrylic polymer adhesive latex emulsion was sprayed onto woven filters and was found to spray well with minimal droplet coalescence and running. After the spray-dried-on filters were installed in a standard home HVAC system, full home air freshness/scent was detected for up to 15 days.

The resulting aqueous scenting formulation meets all regulatory guidelines. And has unique ratios that provide unexpected optimized strength and longevity without the need to add ingredients.

The resulting aqueous scenting formulation containing the vinyl/polyvinyl acetate latex was found to produce excellent grab onto furnace filter fibers and to provide long lasting fragrance release characteristics when the filters were installed in standard home HVAC systems.

Example 3

An aqueous scenting formulation in accordance with the present invention having an "Apple" scent was formulated in the laboratory by mixing the following ingredients:

| | |
|---|---|
| 130 GRS | LANCO JB-100 (POLYVINYL ACETATE BLEND) |
| 80 GRS | HEXYLENE GLYCOL |
| 1 GRS | TROYSAN 174 |
| 48 GRS | TWEEN 20 (POLYSORBATE 20) |
| 610 GRS | WATER |
| 1 GRS | BITREX @ 1% WATER |
| 130 GRS | APPLE FRAG. (APPLE KVJSCENTS #6) |
| 1000 GRS | |

In preparing this composition, the water content of the composition was initially introduced into a main batching vessel at ambient temperature. Then, the vinyl acetate acrylic polymer adhesive latex was added to the water with moderate stirring. Thereafter, remaining ingredients (the surfactant and then the fragrance) were added with continued mixing with an overhead mixer until a homogenous blend was produced.

The resulting aqueous scenting formulation containing the vinyl acetate acrylic polymer adhesive latex emulsion was sprayed onto woven filters and was found to spray well with minimal droplet coalescence and running. After the spray-dried-on filters were installed in a standard home HVAC system, full home air freshness/scent was detected for up to 15 days.

The resulting aqueous scenting formulation meets all regulatory guidelines. And has unique ratios that provide unexpected optimized strength and longevity without the need to add ingredients.

The resulting aqueous scenting formulation meets all regulatory guidelines and has unique ratios that provide unexpected optimized strength and longevity without the need for additional ingredients.

Example 4

An aqueous scenting formulation in accordance with the present invention having a "Peach Blossom" scent was formulated in the laboratory by mixing the following ingredients:

| | |
|---|---|
| 130 GRS | LANCO JB-100 (POLYVINYL ACETATE BLEND) |
| 90 GRS | HEXYLENE GLYCOL |
| 1 GRS | TROYSAN 174 |
| 48 GRS | TWEEN 20 (POLYSORBATE 20) |
| 610 GRS | WATER |
| 1 GRS | BITREX @ 1% WATER |
| 120 GRS | PEACH BLOSSOM FRAG. |
| | (PEACH BLSM KVJSCENTS #7) |
| 1000 GRS | |

In preparing this composition, the water content of the composition was initially introduced into a main batching vessel at ambient temperature. Then, the vinyl acetate acrylic polymer adhesive latex was added to the water with moderate stirring. Thereafter, remaining ingredients (the surfactant and then the fragrance) were added with continued mixing with an overhead mixer until a homogenous blend was produced.

The resulting aqueous scenting formulation containing the vinyl acetate acrylic polymer adhesive latex emulsion was sprayed onto woven filters and was found to spray well with minimal droplet coalescence and running. After the spray-dried-on filters were installed in a standard home HVAC system, full home air freshness/scent was detected for up to 15 days.

The resulting aqueous scenting formulation meets all regulatory guidelines. And has unique ratios that provide unexpected optimized strength and longevity without the need to add ingredients.

The resulting aqueous scenting formulation meets all regulatory guidelines and has unique ratios that provide unexpected optimized strength and longevity without the need for additional ingredients.

Example 5

An aqueous scenting formulation in accordance with the present invention having a "Peach Blossom" scent was formulated in the laboratory by mixing the following ingredients:

| | |
|---|---|
| 120 GRS | LANCO JB-100 (POLYVINYL ACETATE BLEND) |
| 80 GRS | HEXYLENE GLYCOL |
| 1 GRS | TROYSAN 174 |
| 48 GRS | TWEEN 20 (POLYSORBATE 20) |
| 600 GRS | WATER |
| 1 GRS | BITREX @ 1% WATER |
| 120 GRS | PEACH BLOSSOM FRAG. |
| | (PEACH BLSM KVJSCENTS #7) |
| 30 GRS | FLOUR (HOMECRAFT CREATE 765 |
| | NATIONAL STARCH) |
| 1000 GRS | |

In preparing this composition, the water content of the composition was initially introduced into a main batching vessel at ambient temperature. Then, the rheological agent was added with moderate stifling followed by the vinyl acetate acrylic polymer adhesive latex. Thereafter, remaining ingredients (the surfactant and then the fragrance) were added with continued mixing with an overhead mixer until a homogenous blend was produced The resulting aqueous composition containing a mixture of the non-ionic/anionic surfactant and the rheological agent was found to spray well with minimal droplet coalescence and running when sprayed on an air filter in a standard home HVAC system and the filter having the formulation applied thereon demonstrated excellent fragrance release characteristics for at least 15 days.

Example 6

An aqueous scenting formulation in accordance with the present invention having an "Apple" scent was formulated in the laboratory by mixing the following ingredients:

| | |
|---|---|
| 130 GRS | LANCO JB-100 (POLYVINYL ACETATE BLEND) |
| 80 GRS | HEXYLENE GLYCOL |
| 1 GRS | TROYSAN 174 |
| 48 GRS | TWEEN 20 (POLYSORBATE 20) |
| 610 GRS | WATER |
| 1 GRS | BITREX @ 1% WATER |
| 120 GRS | APPLE FRAG. (APPLE KVJSCENTS #6) |
| 10 GRS | FUNGICIDE (POLYPHASE SA 27 TROY CORP) |
| 1000 GRS | |

In preparing this composition, the water content of the composition was initially introduced into a main batching vessel at ambient temperature. Then, the vinyl acetate acrylic polymer adhesive latex was added with moderate stirring. Thereafter, remaining ingredients (the surfactant and then the fragrance) were added followed by the fungicidal agent with continued mixing with an overhead mixer until a homogenous blend was produced.

The resulting aqueous scenting formulation containing the vinyl acetate acrylic polymer emulsion along with a mixture of surfactants and the fungicidal additives was found to produce a barrier film when sprayed on an air filter in a standard home HVAC system and the filter having the formulation applied thereon demonstrated excellent fragrance release characteristics and dust resistance and fungicidal protection over at least 15 days.

Example 7

An aqueous scenting formulation in accordance with the present invention having a "Fresh & Clean" scent was formulated in the laboratory by mixing the following ingredients:

| | |
|---|---|
| 130 GRS | LANCO JB-100 (POLYVINYL ACETATE BLEND) |
| 80 GRS | HEXYLENE GLYCOL |
| 1 GRS | TROYSAN 174 |
| 48 GRS | TWEEN 20 (POLYSORBATE 20) |
| 600 GRS | WATER |
| 1 GRS | BITREX @ 1% WATER |
| 130 GRS | FRESH & CLEAN FRAG. (SIMPLY CLEAN CONC. KVJSCENTS #5) |
| 10 GRS | BLUE DYE (FD&C BLUE #1 @ 1% WATER) |
| 1000 GRS | |

In preparing this composition, the water content of the composition was initially introduced into a main batching vessel at ambient temperature. Then, the vinyl acetate acrylic polymer adhesive latex was added with moderate stirring. Thereafter, remaining ingredients (the surfactant and then the fragrance) were added followed by the blue dye with continued mixing with an overhead mixer until a homogenous blend was produced.

The resulting aqueous scenting formulation containing the vinyl acetate acrylic polymer emulsion along with a mixture of surfactants and the blue dye was found to produce a blue colored barrier film when sprayed on an air filter in a standard home HVAC system and the filter having the formulation applied thereon demonstrated excellent fragrance release characteristics over at least 15 days.

In one or more embodiments, BITREX® at 1 percent water is usable in amount from 0.1 weight percent to 0.2 percent made by Johnson Matthey PLC of London.

In one or more embodiment, the blue dye, known as FD&C Blue #1 at 1 percent water is available from Pylam Products Company, Inc. of Tempe, Ariz., and is usable in amounts from 0.5 weight percent to 5 weight percent.

In one or more embodiments, the starch component can be HOMECRAFT™ Create 765 made by National Starch Food Innovation of Bridgewater, is usable in amounts of 1 weight percent to 8 weight percent based on the total weight of the formulation.

In one or more embodiments, the fragrance can be any of a variety from Abstract Perfumes, Inc. of Suffern, N.Y. and usable in amounts ranging from 10 weight percent to 15 weight percent.

In an embodiment, the surfactant can be Polysorbate 20, which can be commercially purchased as ALKEST® TW 20 and TWEEN® 20.

Polysorbate 20 surfactant has a stability and relative non-toxicity that allows it to be used as a detergent and emulsifier in this application. Polysorbate 20 is a polyoxyethylene derivative of sorbitan monolaurate, and is distinguished from the other members in the polysorbate range by the length of the polyoxyethylene chain and the fatty acid ester moiety.

While these embodiments have been described with emphasis on the embodiments, it should be understood that within the scope of the appended claims, the embodiments might be practiced other than as specifically described herein.

What is claimed is:

1. An aqueous scenting formulation formulated for spray application on air filters for use in an HVAC system, wherein the aqueous scenting formulation comprises:
   a. 10 weight percent to 50 weight percent of a water based vinyl acetate acrylic polymer adhesive latex comprising 40 weight percent to 70 weight percent water, and the water based vinyl acetate acrylic polymer adhesive latex has a mean particle size of a component polymer from 75 microns to 90 microns in diameter;
   b. 0.1 weight percent to 10 weight percent of a low foaming, non-ionic surfactant compatible with anionic particles that additionally act as a wetting agent;
   c. 0.1 weight percent to 10 weight percent of a solvent selected from the group: a glycol, an ethanol, methanol, other alcohols, and combinations thereof; and
   d. 10 weight percent to 40 weight percent of a liquid fragrance capable of dissolving in the solvent;
   wherein the aqueous scenting formulation is blended using high shear mixing for periods of time to form an emulsion latex aqueous scenting formulation using a time period not to exceed 12 hours of mixing;
   wherein the formed emulsion latex aqueous scenting formulation includes a solids content of vinyl/polyvinyl acetate and liquid fragrance content greater than 50 percent by weight of the vinyl/polyvinyl acetate; and
   wherein the aqueous scenting formulation emulsion latex can be applied in a thickness from 1 micron to 50 microns on at least a portion of a filter of an HVAC unit to form a treated filter with an air permeable barrier film, allowing at least 80 percent of the air through the treated filter while reducing a rate of water evaporation through the treated filter by at least 10 percent over a non-treated filter, while simultaneously releasing fragrance into air flowing through the treated filter for up to 15 days.

2. The aqueous scenting formulation of claim 1, wherein the surfactant is a solvent free anionic/nonionic grind aid surfactant.

3. The aqueous scenting formulation of claim 1 wherein the surfactant is selected from the group consisting of: low foaming, non-ionic surfactants compatible with anionic particles, non-ionic, dimethyl octynediol surfactants, ethoxylated alkyl phenols, non-ionic, octoxynol 9 surfactants, non-ionic, polysorbate 20 and mixtures thereof.

4. The aqueous scenting formulation of claim 1, further comprising 0.1 weight percent to 8 weight percent of a rheological modifier.

5. The aqueous scenting formulation of claim 4, wherein the rheological modifier is selected from the group consisting of: gums, clays, cellulosic material, sugars, starches, algins, polymeric thickeners, and mixtures thereof.

6. The aqueous scenting formulation of claim 1, further comprising from 0.1 weight percent to 0.5 weight percent of an antimicrobial agent comprising: an antifungal component, an antibacterial component, or combinations thereof, for reducing the presence of microbes on an air filter coated with the aqueous scenting formulation.

7. The aqueous scenting formulation of claim 1, wherein the spray application is a non-aerosol spray.

8. The aqueous scenting formulation of claim 1, further comprising from 0.1 weight percent to 1 weight percent of a mildewcide.

9. The aqueous scenting formulation of claim 1, wherein the surfactant can additionally contain from 0.1 weight percent to 2 weight percent of detergents, wetting agents, emulsifiers, foaming agents, and dispersants.

10. The aqueous scenting formulation of claim 1, further comprising from 0.1 weight percent to 8 weight percent of a pigment, fillers, and malodor scavengers.

11. An HVAC air filter having at least one surface at least partially covered with the formulation of claim 1.

* * * * *